United States Patent [19]
Quinn

[11] Patent Number: 5,924,865
[45] Date of Patent: Jul. 20, 1999

[54] CHUCK WITH A PUSH BUTTON RELEASE FOR A DENTAL/MEDICAL DEVICE

[75] Inventor: Michael J. Quinn, Wildwood, Mo.

[73] Assignee: Young Dental Manufacturing Company, Earth City, Mo.

[21] Appl. No.: 08/928,549

[22] Filed: Sep. 12, 1997

Related U.S. Application Data

[51] Int. Cl.[6] .................................................... A61C 1/14
[52] U.S. Cl. ........................................................... 433/127
[58] Field of Search ................................ 433/127, 128; 279/76, 79

[56] References Cited

U.S. PATENT DOCUMENTS

| | | | |
|---|---|---|---|
| 2,791,835 | 5/1957 | Staunt | 433/128 |
| 3,413,578 | 11/1968 | Dennison | 335/167 |
| 4,014,099 | 3/1977 | Bailey | 433/128 |
| 4,370,132 | 1/1983 | Wohlgemuth | 433/128 |
| 4,398,886 | 8/1983 | Schuss et al. | 433/128 |
| 4,661,062 | 4/1987 | Seigneurin | 433/128 |
| 4,975,056 | 12/1990 | Eibofner | 433/84 |
| 5,028,181 | 7/1991 | Jenkins et al. | 409/215 |
| 5,037,299 | 8/1991 | Nakanishi | 433/128 |
| 5,090,906 | 2/1992 | Pernot | 433/127 |
| 5,435,979 | 7/1995 | Miller et al. | 433/77 |

FOREIGN PATENT DOCUMENTS

| | | |
|---|---|---|
| 0037021 | 10/1981 | European Pat. Off. . |
| 2905484 | 8/1979 | Germany ................................ 433/127 |
| 2918816 | 12/1979 | Germany ................................ 433/128 |

*Primary Examiner*—John J. Wilson
*Attorney, Agent, or Firm*—Polster, Lieder, Woodruff & Lucchesi

[57] ABSTRACT

A medical/dental device is provided which includes a body having a hollow sleeve and a head at an end of the sleeve. The head defines an upwardly opening chamber which receives a chuck. The chuck includes a bur tube which removably receives a medical/dental tool of the latch-shaft type and a push button actuator to release the shaft from the bur tube. The bur tube includes a flexible arm which extends above the bur tube's upper surface and an inwardly extending finger positioned to engage the groove of the shaft. A resilient member (preferably a leaf spring) is received in a transverse slot formed in the top of the bur tube body and is retained in place by a retainer key. The shoulder of the latch-type bur abuts the bottom of the spring to reduce axial play of the bur and to allow for use of non-standard burs in the bur tube. The push button includes a downwardly extending pedestal which engages the arm to move the arm from a first position in which the groove and the finger create an interference fit to prevent the shaft from being removed from the head to a second position in which the finger is disengaged from the groove to allow removal of the shaft.

26 Claims, 7 Drawing Sheets

FIG. 12

CHUCK WITH A PUSH BUTTON RELEASE FOR A DENTAL/MEDICAL DEVICE

RELATED APPLICATION INFORMATION

This invention disclosed herein is related to the invention disclosed in my co-pending application Ser. No. 08/648,817, filed May 16, 1996, now U.S. Pat. No. 5,704,786 entitled CHUCK WITH A PUSH BUTTON RELEASE FOR A DENTAL/MEDICAL DEVICE, and which is incorporated herein by reference.

BACKGROUND OF THE INVENTION

This invention relates to medical/dental handpieces, and in particular to a chuck of a medical/dental handpiece which removably receives tools having latch-type shafts and which has a push button release to allow easy removal of the tool from the handpiece.

Dental handpieces include both high speed turbine types (typically 200,000 to 400,000 rpm) having an air motor and gear-driven lower speed types (typically, 1,000 to 30,000 rpm) having an air motor or an electrical motor. Both have long employed chucks for releasably holding dental burs which cut, grind and polish teeth. Similar burs are used in surgery for performing these functions on bone. Because the shafts of dental tools are quite small and quite closely toleranced (latch-type shaft diameters are typically between 0.0919" and 0.0925"), and because the demands of dental and surgical procedures require the utmost performance, chucks for medical and dental instruments are high precision devices requiring a great deal of care and expense in their manufacture.

There are essentially two types of shafts that are provided on dental/medical burs. One is a generally straight smooth shaft which is typically frictionally held by the chuck. This is sometimes referred to as a friction grip shaft and is made in accordance with ANSI/ADA spec. No. 23 for a Class 4 bur. The other is a shaft having a radial groove formed near its top end and a flat edge extending downwardly from its top. At the bottom of the flat edge, the shaft forms a shoulder. This is typically referred to as a latch-type shaft and is a Class 2 bur. In handpieces which accept latch-type shafts, the handpiece typically includes a bar or lever in the top of the handpiece head which swings horizontally relative to the sleeve of the handpiece (when the handpiece is held with the bur extending downwardly). The lever includes a slot which engages the groove in the bur shaft to hold the bur in the handpiece. When the lever is swung outwardly from the sleeve of the handpiece, the lever's slot is disengaged from the groove in the shaft of the latch bur. The bur may then be removed from the handpiece. The formation of the lever in the head requires that a slot be formed in the head. This creates an opening into the head which will allow contaminants and debris to enter the head. Such contaminants and debris are difficult to fully clean from the handpiece. The debris can include items such as dental matter, amalgam, bone, etc. If the debris is not cleaned from within the head of the handpiece, it will abrade the gears which drive the bur, and substantially shorten the working life of the handpiece. Further, if the contaminants (such as saliva, blood, etc.) are not properly cleaned from the handpiece, the handpiece will not be properly sterilized.

In my co-pending application, Ser. No. 08/648,817, filed May 16, 1996, now U.S. Pat. No. 5,704,786, which is incorporated herein by reference, I disclose a push button chuck for use with latch type burs. The operation of the chuck relied on the bur having a standard shaft which conforms to the standards for Class 2 burs. However, in testing the chuck, I have found that a high percentage of burs do not conform to the standard for Class 2 burs. In these burs, the distance between the axial shoulder and the groove does not correspond to the standard distance as set forth in ANSI and ADA standards. The chuck of the above noted application relied on this distance complying with the ANSI and ADA standards. Thus, burs which did not comply with the standards would not work well with that chuck.

SUMMARY OF THE INVENTION

One object of the present invention is to provide a simple, effective chuck for releasably holding a dental tool in a handpiece.

Another object is to provide a release mechanism for the chuck which is easy to operate.

Another object is to provide a chuck which will accept non-standard latch-type burs.

These and other objects will become apparent to those skilled in the art in light of the following disclosure and accompanying drawings.

In accordance with the invention, generally stated, a medical/dental device is provided which includes a body having a hollow sleeve and a head at an end of the sleeve. The sleeve receives a drive mechanism. The head defines an upwardly opening chamber having an upwardly opening mouth and a floor. An opening is formed in the floor and is sized to admit the passage of a shaft of a medical/dental instrument. The medical/dental instrument is of the type wherein the shaft has an axis, an axially extending flat extending downwardly from a top of the shaft, a shoulder at the bottom of the flat which is perpendicular to the shaft axis, and a groove spaced from the top of the shaft which is perpendicular to the flat. The groove is defined by upper and lower surfaces and at least the groove upper surface is perpendicular to the axis of the shaft.

A bur tube is received in the head chamber. The bur tube includes a bur tube body having a top surface and a bore which extends through the body sized to receive the shaft. A transverse slot is formed in the wall of the bur tube body which receives a resilient member and a retaining key. The transverse slot, which is the depth of the bur tube body wall, is sized to accept the retaining key. The retaining key defines an inner chamber which receives the resilient member. The resilient member extends into the bur tube body bore from the wall of the bur tube body and the key is fixed to the body to hold the resilient member in place. The resilient member is preferably a leaf spring which takes the shape of a "U" when placed in the bur tube. The top of the bur tube forms a "D" hole which opens into the bur tube bore. The "D" hole is sized to receive the flat of the shaft to rotationally fix the shaft relative to the bur tube such that rotation of the bur tube will rotatably drive the shaft. The shaft extends above the top of the bur tube and the shaft groove therefore is spaced above the bur tube upper surface. When the shaft is received in the bur tube, the shoulder of the shaft abuts the bottom surface of the resilient member.

The bur tube includes a flexible arm which extends above the upper surface of the bur tube and has an inwardly extending finger positioned below the top of the arm to engage the shaft groove. The arm is movable between a first position in which the groove and the finger create an interference fit to prevent the shaft from being removed from the head and a second position in which the finger is disengaged from the groove to allow removal of the bur.

An axial slot is formed in the wall of the bur tube and extends downwardly from a top of the wall. The arm is positioned in the axial slot, extends upwardly from the bottom of the axial slot, and, preferably, is integrally formed with the bur tube. Preferably, the axial slot extends through the wall of the bur tube such that an inner surface of the arm defines a portion of an inner surface of the bur tube. The arm has a thickness which, at least in part, is narrower than the bur tube wall. The arm can be divided into three portions. At the bottom of the arm, at the bottom of the axial slot, the arm has a thickness substantially equal to the thickness of the bur tube wall. Above this first portion, the arm has a thickness that is narrower than the width of the bur tube wall. This second portion of the arm extends to the finger. The outer surface of the arm includes a curved area which forms the transition between the first and second portions of the arm. Above the finger, the arm has a thickness narrower than the second portion of the arm.

The finger has a flat upper surface and a sloped lower surface which are joined by a generally vertical wall. At the base of the finger, where the finger is attached to the arm, the finger has a height that is approximately equal to the height of the groove in the shaft of the dental/medical tool. The flat upper surface of the finger is adjacent the flat or horizontal upper surface of the shaft when the finger is engaged with the groove. Thus, the shaft cannot be removed when the finger is engaged with the groove. The shaft has a beveled edge at the top thereof which interacts with the sloped lower surface of the finger to urge the finger and the arm radially outwardly when the bur shaft is inserted into the bur tube. The arm snaps from the second position to the first position when the groove comes into alignment with the finger.

The shaft has a distance "a" between the shaft shoulder and the top surface of the groove. Similarly, the bur tube has a distance "b" between the bottom surface of the spring and the top surface of the finger. Ideally, for a shaft which complies with the standards noted above, the distance "a" is slightly smaller than the distance "b" so that the spring will be slightly deflected when the shaft is inserted in the bur tube. However, if the distance "a" of a chosen shaft is out of standard, and is shorter than the distance "a" of a standard shaft, the shaft will still be able to be received in the bur tube—the shaft will simply deflect the spring more. Similarly, if the distance "a" of a chosen shaft is longer than the distance "a" of a standard shaft, the shaft will still be able to be received in the bur tube—in this instance, there will be less deflection of the spring. Thus, shafts which do not comply with the standard distance "a" can still be used in the bur tube of the present invention.

A cap or ring is received in the mouth of the head and has an upper opening. A push button actuator is received in the cap for axial movement relative to the cap and extends through the cap upper opening to be operable by a user of the medical/dental device. The push button actuator includes a top, an annular wall depending from the top, and a pedestal depending from the push button top inside of the annular wall. The push button is selectively movable between a first position in which the pedestal is spaced from the upper portion of the bur tube arm and a second position in which the pedestal engages the upper portion of the bur tube arm to move the arm from the arm's first position to the arm's second position. The push button is biased to its first position, preferably by a deformable silicone disk, although a spring or spring washer could also be used.

The pedestal defines a truncated cone and has a sloped side. The bur tube arm has a sloped upper surface which is engaged by the sloped side of the pedestal when the push button is pressed. Preferably, the sloped side of the pedestal has a length greater than the sloped surface of the arm upper portion. When the push button is pressed, the sloped side of the pedestal engages the sloped surface of the arm to move the arm between the first and second positions. A bore or depression is formed in the lower surface of the pedestal and is sized to prevent the top surface of the bur shaft from contacting the pedestal when the push button is moved to its second position.

DESCRIPTION OF THE PREFERRED EMBODIMENT

Figure 1:
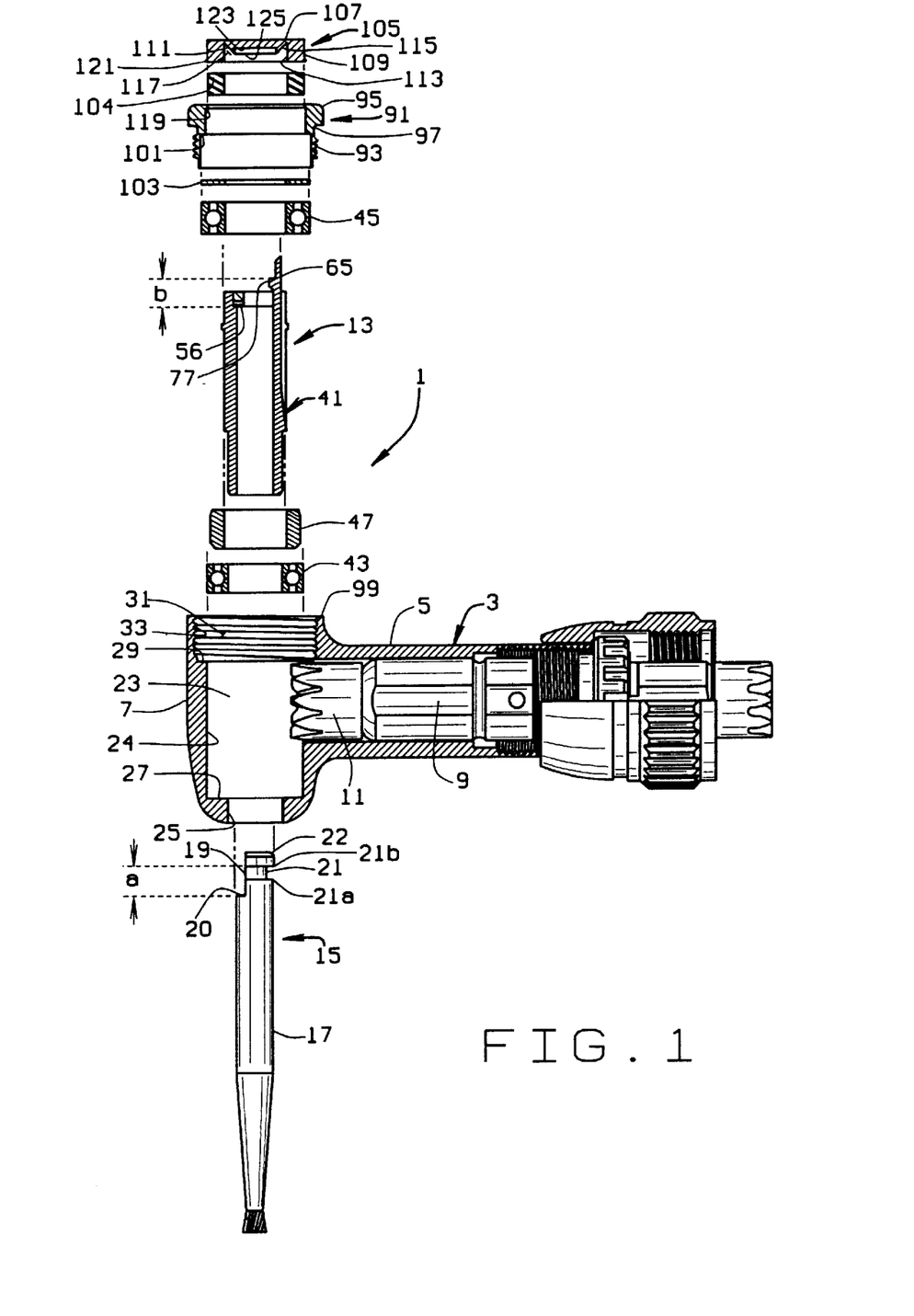
FIG. 1 is an exploded, cross-sectional view of a dental/medial handpiece including a chuck of the present invention.
Figure 10:
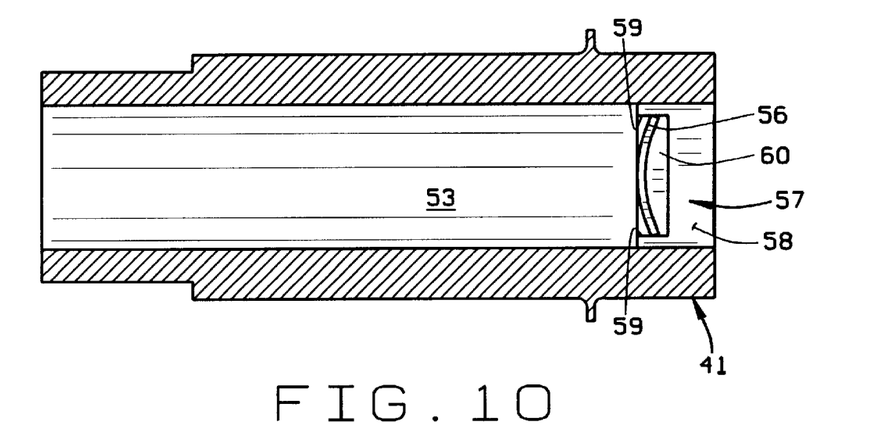
FIG. 10 is a cross-sectional view taken along line 10—10 of FIG. 7.

A handpiece 1 of the present invention is generally shown in FIGS. 1–5. The handpiece 1 includes a body 3 having a hollow sleeve 5 and a hollow head 7. The sleeve 5 receives a drive member 9 having a drive gear 11 at the end thereof. The handpiece 1 is mounted on a handpiece drive (as is known) and the drive member 9 is operatively connected to the handpiece drive to be rotationally driven by the handpiece drive. A chuck 13 is received in the head 7 of the handpiece 1. Chuck 13 receives a bur 15 which has a shaft 17. As best seen in FIGS. 1 and 10, the shaft 17 has an axially extending flat 19 extending down from a top surface of the shaft. The shaft has a shoulder 20 at the bottom of the flat 19. A groove 21 is formed near the top of the shaft 17 spaced from the shoulder 20. The groove 21 is a circumferential or radial groove which is generally perpendicular to the axis of the shaft and to the flat 19, and is defined by upper and lower surfaces 21a,b. The groove surfaces 21a,b are generally perpendicular to the axis of the shaft 17. The top surface of the shaft preferably has a beveled or rounded edge 22.

The head 7 of the handpiece 1 defines an upwardly opening chamber 23 defined by a generally cylindrical wall 24 which receives the chuck 13. An opening 25 is formed in the floor 27 of the chamber. Opening 25 is sized to receive the bur shaft 17. Near the top of the head 7, the wall 24 is stepped, as at 29, to define an area 31 having an internally threaded wall 33. The threaded wall 33 has a greater diameter than the wall 24.

Figure 12:
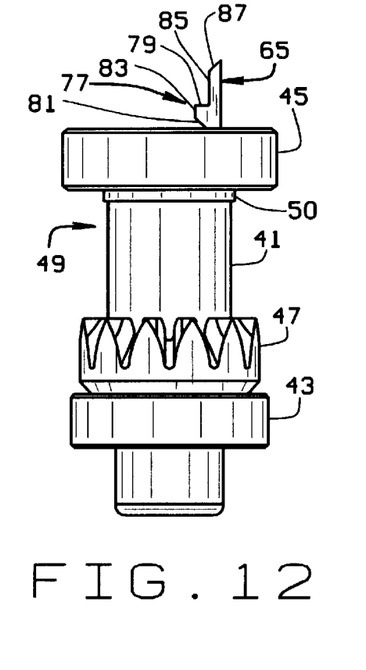
FIG. 12 is an elevational view of a bur tube assembly which includes the bur tube.

The chuck 13 includes a bur tube 41 and a push button actuator 95. The bur tube 41 is journaled in a bottom bearing 43, a top bearing 45, and a driven gear 47. The bearings 43 and 45 and the driven gear 47 are all generally annular and are press-fit onto the bur tube 41. The bur tube 41, bearings 43 and 45, and driven gear 47 form a bur tube assembly 49 (FIG. 12).

Figures 6, 7, 8, 9:
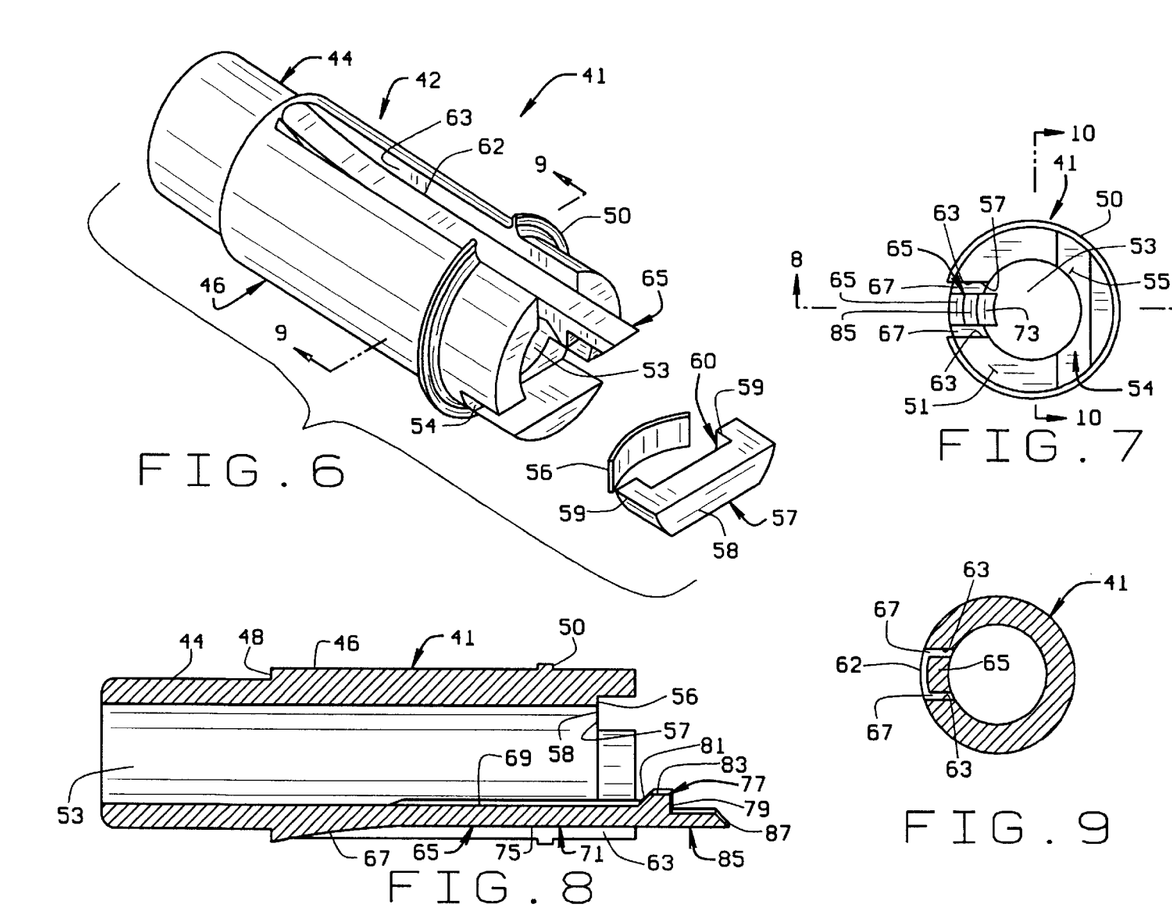
FIG. 6 is an exploded perspective view of a bur tube of the chuck.
FIG. 7 is a top plan view of a body of the bur tube.
FIG. 8 is a cross-sectional view of the bur tube taken along line 8—8 of FIG. 7.
FIG. 9 is a cross-sectional view of the bur tube taken along line 9—9 of FIG. 6.

The bur tube 41 is shown in detail in FIGS. 6–1. The bur tube 41 includes a bur tube body 42 having a lower section 44 which has an outer diameter sized to be press fit in the lower bearing 43 and an upper section 46 which has an outer diameter sized to be press fit in the driven member 47 (such as a gear or a turbine) and the upper bearing 45. Alternatively, the driven member could be laser welded to, or integrally formed with, the bur tube 41. The bur tube body's lower section 44 has a smaller diameter than the upper section 46, and the two sections define a step or shoulder 48. The shoulder 48 provides a stop to prevent the driven member 47 from being pressed too far onto the bur tube 41. As can be seen in FIG. 12, when the gear 47 is pressed onto the bur tube, the gear is adjacent the top of the lower bearing 43. A ring or shoulder 50 is formed around the upper section 46 spaced from the top 51 of the bur tube 41. The ring 50 provides a seat on which the upper bearing 45 sits when the bearing 45 is press fit on the bur tube body 42. A cylindrical bore or passage 53 of substantially constant diameter extends through the bur tube 41. The bore 53 is sized to slidably receive the shaft 17 of the bur 15. A transverse slot 54 extends downwardly from the top 51 of the bur tube body 42. The slot 54 has a bottom surface 55.

The bur tube 41 also includes a leaf spring 56 and a retainer key 57. The leaf spring 56 is received in the transverse slot 54 and rests on the slot bottom surface 55. As seen, the leaf spring 56 is generally U-shaped, and is positioned in the slot 54 so that its ends are spaced from the slot bottom surface 55. The retainer key 57 is received in the slot 54 above the leaf spring 56. The retainer is sized and shaped to close the slot, and is welded, glued, or otherwise fixed, in place in the slot 54. As best seen in FIG. 6, the retainer key 57 has a top 58 which extends across the slot 54 and a pair of legs 59 which depend downwardly from the top 58. The legs 59 and top 58 fully close the slot 54 and cooperate to create a chamber 60 which receives the spring 56. Thus, the spring 56 is not exposed, and cannot be seen from the outside of the bur tube 41. As seen, the outer surfaces of the retainer key 57 have the same curvature as the outer surface of the bur tube body 42 such that when the key 57 is welded in place in the bur tube body 42, the outer surface of the bur tube 41 will be substantially smooth.

The retaining key 57 partially closes the bur tube bore 53. It has a flat inner surface, such that when the retainer key 57 is in place, the top of the bur tube 41 has a "D" hole 61 which partially closes the bore 53.

Figure 11:
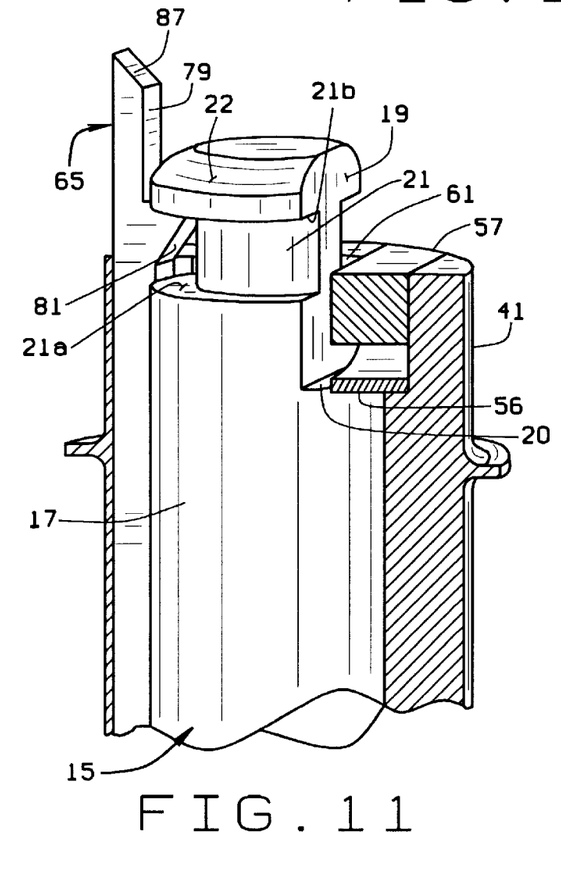
FIG. 11 is a perspective view, partially cut-away, showing the latch-type bur received in the chuck.

As seen in FIG. 11, the spring 56 extends into the bur tube bore 53. When the bur 15 is placed in the bur tube 41, the surface 20 of bur shaft 17 abuts the bottom of the spring 56 when the bur is fully received in the bur tube 41. The flat 19 extends through the "D" hole 61 and the flat 19 and the "D" hole 61 interact to rotationally fix the bur 15 with respect to the bur tube 41. Thus, when the bur tube is rotated, the bur 15 will also rotate.

An elongate axial slot 62 (FIG. 6) is formed in the bur tube body upper section 46. The slot 61 is defined by side walls 63 and extends from the top of the bur tube body nearly to the bur tube body's shoulder 48. A flexible arm 65 extends the from the base of the slot 62 up past the top 51 of the bur tube 41. The arm 65 has a circumferential width that is less than the circumferential width of the slot 62. The arm 65 thus defines spaces or gaps 67 (FIG. 7) with the side walls 63 of the slot 62. The arm 65 has a inner surface 69 and an outer surface 71. The inner surface is shaped to match the curvature of the bur tube's inner surface. At the base of the arm, the arm 65 has a thickness equal to the thickness of the bur tube body wall. The outer surface of the arm 65 curves radially inwardly, as at 73, from the base of the arm for a short distance such that the arm goes from having a width substantially equal to the width of the bur tube body wall to a width that is narrower than the bur tube body wall. The outer surface of the arm then becomes generally straight, as at 75, where the thickness of the arm is about ½ the thickness of the wall of the bur tube body 42. The arm 65 is formed integrally with the bur tube body 42, such that the bur tube body 42 and the arm 65 form a one-piece, unitary component of the handpiece.

Figure 2:
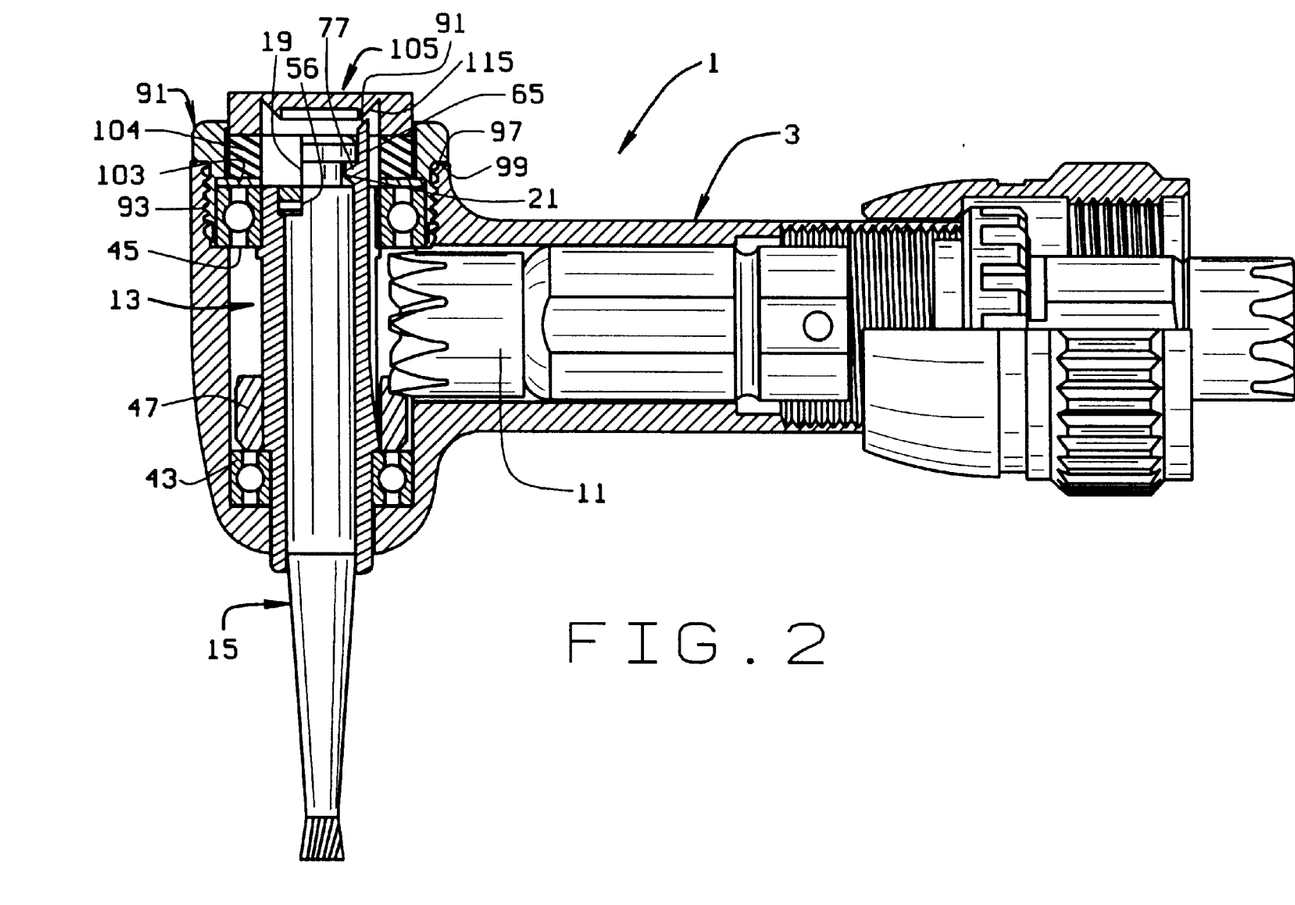
FIG. 2 is a cross-sectional view of the handpiece, the chuck securely holding a bur therein for use.

An inwardly directed finger 77 is spaced from the top of the arm 65 and above the top 51 of the bur tube body 42. The finger 77 is preferably integrally formed with the arm 65. The finger 77 has a flat upper surface 79 and a sloped lower surface 81 connected by a generally vertical side surface 83. The finger 77 is sized to be received in the groove 21 of the bur shaft 17, as seen in FIG. 2 when the shaft is inserted in the bur tube to secure the shaft in the handpiece 1. As also seen in FIG. 2, the height of the finger, at the base of the finger, is about equal to the height of the shaft groove 21. The side surface 83, at the end of the finger, has a height equal to about ½ to ¾ of the height of the groove 21. The finger is spaced beneath the top of the arm 65, and the portion 85 of the arm 65 which extends above the finger 77 is thinner than the remainder of the arm and has a sloped top surface 87.

Turning back to FIG. 1. the opening 31 of the head 7 receives a generally cylindrical and open cap or ring 91 which has an externally threaded stem 93. The stem 93 is hollow and open at its bottom. The stem 93 is screwed into the opening 31 of the head to secure the cap 91 to the head. The cap has an outwardly extending flange 95 which forms a shoulder 97 with the stem 93. When the cap 91 is screwed into the head 7, the cap shoulder 97 is adjacent the top surface 99 of the head 7, as seen in FIG. 2. The inner diameter of the stem 93 is sufficiently wide to receive the upper bearing 45. The cap 91 includes an inner shoulder 101 at the top of the stem 93. As seen in FIG. 2, a washer 103 is disposed between the top surface of the upper bearing 45 and the cap's inner shoulder 101. A spring 104 is positioned on the washer 103. The spring 104 is preferably a washer of a compressible material, such as silicone. The spring 104, however, could also be a spring washer or a spiral spring. The washer 103 has an outer diameter greater than the inner diameter of the cap to be captured between the cap shoulder 101 and the upper bearing 45.

The cap 91 receives a push button actuator 105 which extends up out of the cap 91 and slides axially with respect to the cap. The push button 105 has a generally flat top 107, an annular wall 109, and an internal pedestal or member 111 extending downwardly from the inner surface of the cap top 107. The pedestal 111 is concentric with the wall 109. The cap wall 109 has a generally circular inner surface 113. The pedestal forms a truncated cone and has an upwardly and radially outwardly sloped side surface 115 which intersects the inner surface 113 at the top thereof. The surface 115 and wall 109 define a generally triangularly shaped area 117.

The cap has a small inwardly extending lip 119 and the push button has a outwardly extending flange 121 at the base of its wall 109. The cap lip 119 and push button flange 121 cooperate to maintain the push button 105 in the cap 91 so that the push button 105 does not come out of the cap 91. The silicone disk 104, which is received in the cap 91, operates to bias the push button actuator 105 normally upwardly.

The operation of the chuck 13 is shown in FIGS. 2–5. In FIG. 2, the handpiece is shown in its operating condition. The shoulder 20 of the shaft 17 abuts the bottom of the spring 56, and the finger 77 of the flexible arm 65 is received in the groove 21 of the bur shaft 17. The flat top surface 79 of the finger 77 is adjacent the flat top surface of the groove 21. The groove 21 and finger 77 create an interference fit to prevent the bur 15 from being pulled out of the handpiece 1. In this operating position, the top surface 87 of the bur tube arm 65 is spaced from the pedestal 111 of the push button 105.

Figure 3:
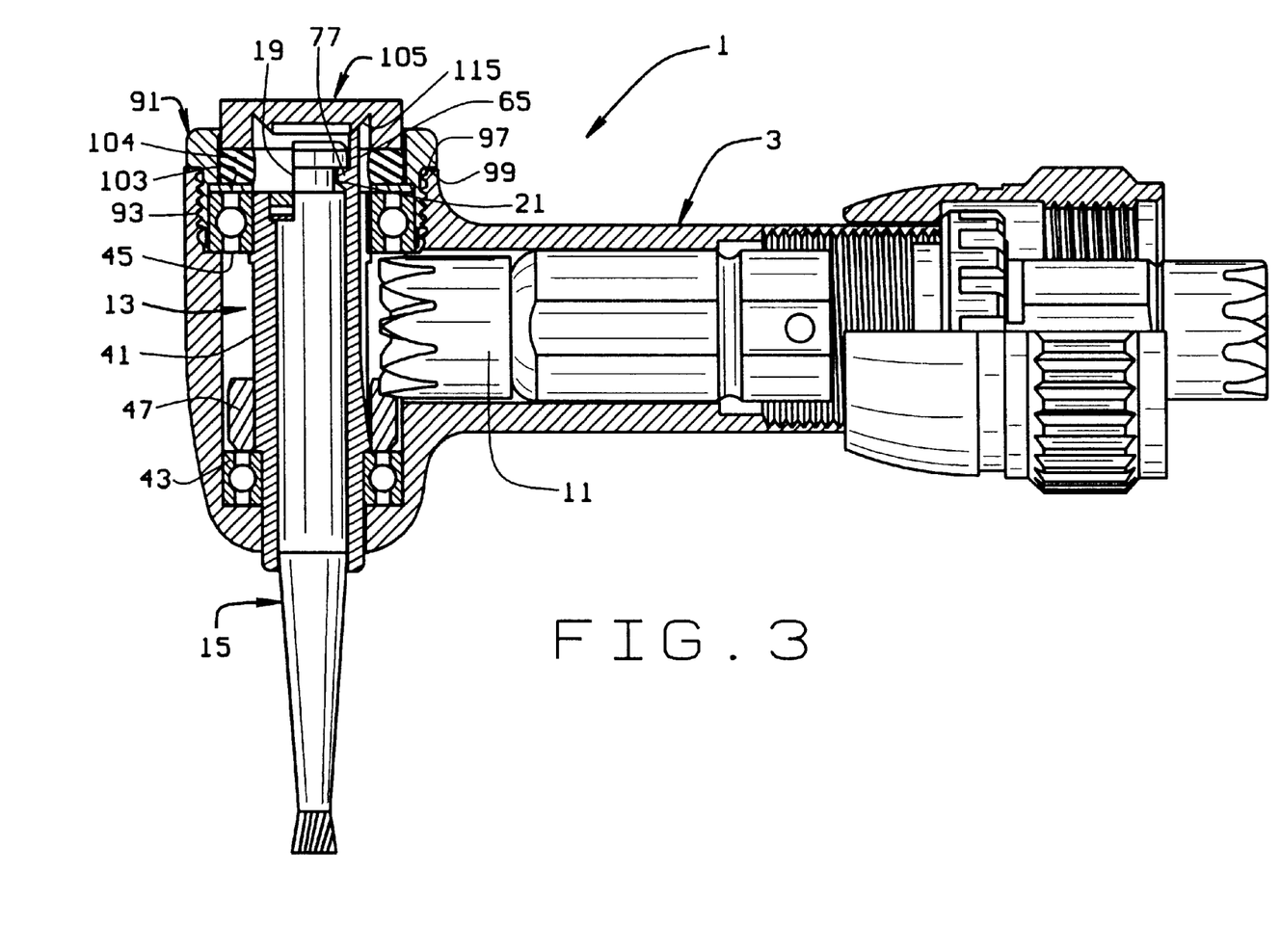
FIGS. 3–5 are similar to the view of FIG. 2, but show the operation of a push button release mechanism of the chuck to easily remove the bur from the handpiece.

In FIG. 3, the push button actuator 105 is shown pushed downwardly to a point where the sloped surface 115 of the pedestal 111 is in contact with the sloped surface 87 of the bur tube arm 65. As can be seen, the surfaces 115 and 87 have complimentary slopes so that they will slide against one another. Further, the pedestal surface 115 is longer than the arm surface 87 so that the arm 65 does not fill the space 117 between the pedestal 111 and the inner surface 113 of the push button wall 109. The surfaces 87 and 115 can thus slide against each other.

Figure 4:
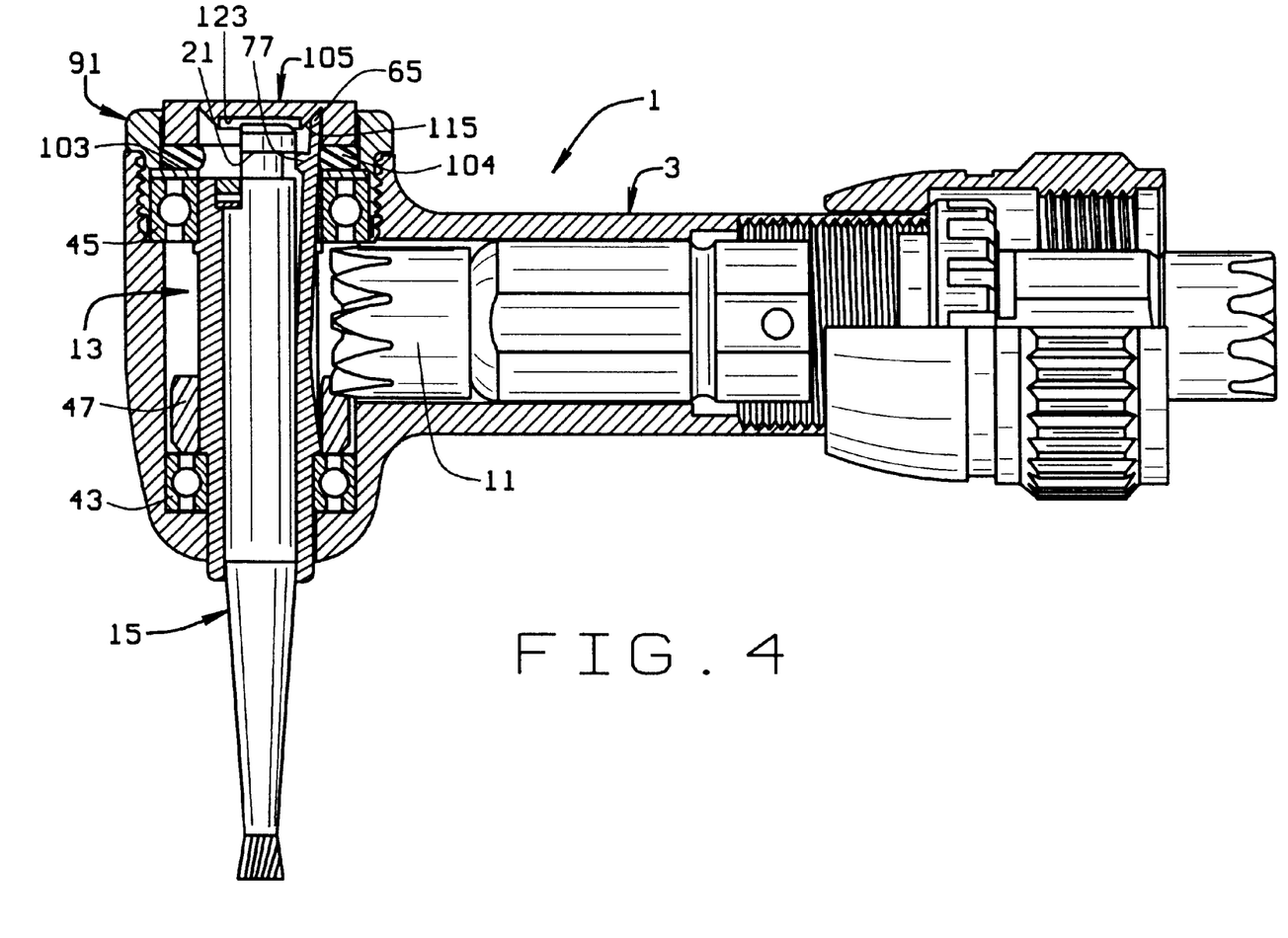
Figure 5:
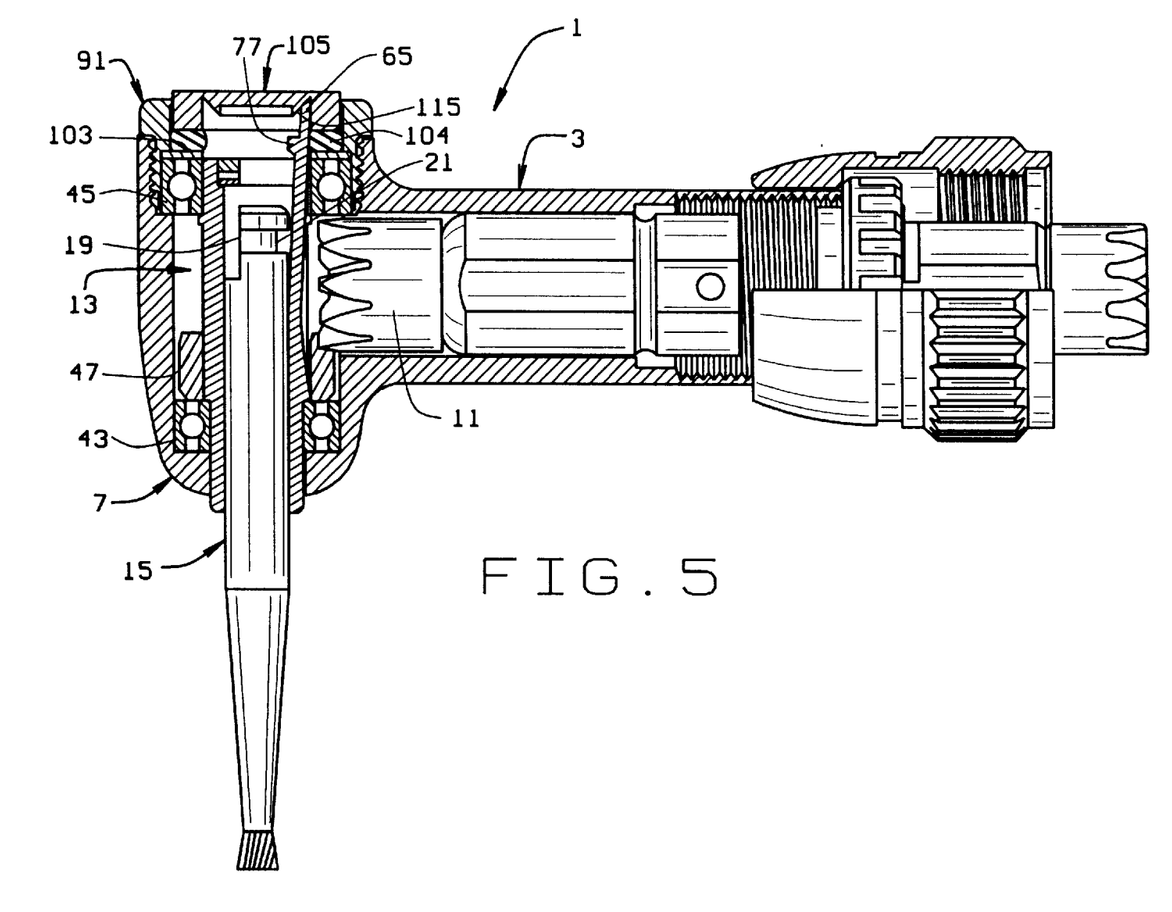

In FIG. 4, the push button actuator 105 is pushed down farther. When the push button is continued to be pushed down, as shown in FIG. 4, the interaction of the surfaces 87 and 115 cause the pedestal to push the arm 65 radially outwardly to move the finger 77 out of the shaft groove 21. The pedestal surface 115 and the finger 77 are sized such that when the push button 105 is fully depressed, the finger 77 will be fully disengaged from the groove 21 of the bur 15. When the finger 77 is disengaged from the bur groove 21, the bur may be pulled out of the handpiece head 7, as shown in FIG. 5.

As can be seen (in FIGS. 1–5), the pedestal 111 has a bore 123 formed in its lower surface 125. The bore 123 is sized in diameter and depth to receive the top of the bur shaft 17 to prevent the bur shaft 17 from contacting the bottom of the pedestal 111. If the bottom of the pedestal were to contact the top of the bur shaft, the finger may not be able to be fully disengaged from the groove 21. This result could also be achieved by other means, for example by changing the sizes of the arm portion 85 above the finger 77 and the push button 105.

To insert a bur into the head 7, the bur shaft is simply pushed into the head. The beveled or curved edge 22 of the shaft 17 will interact with the sloped surface 81 of the finger 77 and push the finger radially outwardly as the shaft 17 is urged past the finger. When the groove 21 comes into alignment with the finger 77, the arm 65 will spring back and the finger 77 will engage the groove 21 to secure the bur 15 in the handpiece 1. Although the bur may need to be rotated to pass the flat of the bur through the "D" hole 61, the operation of the chuck 13 allows for the bur to be inserted into the chuck without the need to depress the push button 105. There is thus no latch, button, or other mechanism that need be actively operated by the dentist, as is required by the chucks presently available, to secure latch-type bur shafts in the chuck.

The thinness of the arm 65 provides resiliency to the arm and creates an arm that does not need undue force to be flexed outwardly. If the arm 65 had a thickness as thick as the wall of the bur tube 41, the chuck would be more difficult to operate. Further, the narrowing of the arm prevents the arm from contacting the inner race of the upper bearing 45. As can be appreciated, the bearing 45 surrounds the bur tube 41. If the arm 65 were as thick as the bur tube wall, the arm would not be able to be deflected outwardly, and the chuck thus would not be operable to either accept or release a bur.

As can be seen in FIG. 2, when the bur 15 is received in the bur tube 41, the surface 20 of the bur shaft 17 abuts the spring 56 and the finger 77 of the bur tube arm 65 is received in the bur shaft groove 21. The spring 56 will thus exert a downward force on the shaft 17. This downward force reduces or eliminates any axial play that may be present in the shaft when it is received in the bur tube 41. As can be appreciated, there are two distances which are important in the manufacture of the bur tube 41. The first is the distance "a" (FIG. 1) between the shoulder surface 20 and the groove upper surface 21 in the bur shaft 17. The second distance "b" is the distance between the bottom of the spring 56 and the surface 79 of the arm finger 77. Preferably, the distance "a" of a shaft which complies with the requisite standards will be slightly smaller than the distance "b" of the bur tube. Thus, the spring will be depressed or deflected when a standard shaft is introduced into the bur tube to reduce or eliminate axial play as noted above. As can be seen in FIG. 11, there is a gap between the surface of the spring and the retainer key 57. Therefore, the spring can be deflected to a greater extent. This allows for the bur tube 41 to accept a shaft which has a distance "a" that is shorter than the standard distance "a". In this case, the spring 56 will be depressed or deflected further than for a standard shaft, and the bur shaft groove 21 will be able to be brought into alignment with the bur tube finger 77 to hold the bur 15 in the bur tube 41. In the instance where the distance "a" of a selected shaft is longer than the distance "a" of a standard shaft, the shaft can still be received in the bur tube 41 of the present invention as long as the distance "a" is not longer than the distance "b" of the bur tube. In this case, the spring will simply be deflected to a lesser extent than when a standard shaft is placed in the bur tube.

As can be appreciated, the chuck provided by the present invention securely holds a standard, or non-standard, latch-type bur shaft in a handpiece so that the bur may be driven by the handpiece. The use of the spring 56 allows for greater latitude in the bur shafts which can be accepted in the bur tube 41. Further, the use of the spring 56 or a resilient member which achieves the same function reduces the need to maintain tight tolerances in the manufacture of the bur tube 41. The ability to increase the tolerances acceptable in the part reduces the cost of manufacturing the part.

As can also be appreciated, the push button release of the chuck is easy to operate and allows for simple and easy insertion and removal of burs from the handpiece 1. Further, the push button 105 and cap 91 effectively seal or close the head 7 of the handpiece. There are no openings or gaps large enough through which debris can enter the head of the handpiece. The effective life of the handpiece thus will not be reduced, as occurs with handpieces currently available which include gaps through which debris can enter the handpiece head. The push button and cap also substantially prevent contaminants, such as saliva, from entering the head. If such contaminants do enter the head, the handpiece can be sterilized, such as in an autoclave.

As variations within the scope of the appended claims may be apparent to those skilled in the art, the foregoing description is set forth only for illustrative purposes and is not meant to be limiting. For example, the gear 47 could be replaced with a turbine and the drive 9 and drive gear 11 can be replaced with a system for delivering an operating fluid (typically air) to the head such that the bur would be fluid driven rather than gear driven. The arm 65 need not be as long as the upper portion of the bur tube. The arm need only be long enough to allow it to be sufficiently flexible to move between a position in which its finger engages the shaft groove and a position in which the finger is disengaged from the shaft groove. The axial slot 62 in which the arm is positioned need not extend completely through the wall of the bur tube. The arm 65 could be of a uniform depth, and there could be a step between the arm and the base of the slot, instead of the sloped surface 73. The sloped surface 87 of the arm 65 could be replaced with a sharp corner or edge, and this edge would then be contacted by the sloped surface of the pedestal. Alternatively, the pedestal could have a sharp edge and the arm could include the sloped surface 87. In these variations, the arm will be urged outwardly by the interaction of a sloped surface and an edge or corner. Although the flat on the bur shaft and the "D" hole in the bur tube are preferred to rotationally fix the bur shaft with respect to the bur tube, other means could be used. The shaft could simply be frictionally held in place. Alternatively, the bur shaft and bur tube could have axially extending ribs and grooves which cooperate to rotationally fix the bur shaft in the bur tube so that the shaft is rotated by the bur tube. The bur tube is describe to have a "D" hole when the retaining key is fixed in its slot. This "D" hole could be replaced with any opening have a straight, for example a hexagonal or octagonal head. The opening in the top of the bur tube need only be shaped complementary to the shape of the top of the bur shaft to prevent the bur shaft from rotating relative to the bur tube. Although the arm 65 extends above the bur tube's top surface, the bur tube could be extended so that the top of the bur tube is level with or even above the top of the arm 65. The spring 56 could be replaced with a resilient member, such as a rubber member, which will have the same biasing effect. The biasing member can be a leaf spring, as shown in the drawings, or it could comprise a strip of resilient material which is received in the transverse slot 43. Alternatively, the spring could be replaced with a resilient washer having an opening shaped to allow the top of the bur shaft 17 to pass through the washer. Such a washer could be a washer made of resilient material having a hole therein so that the shoulder 20 of the shaft 17 will abut the bottom surface of the washer when the bur is received in the bur tube 41. The leaf spring could also be replaced with a coiled spring. In either a case, rather than having a transverse slot, a counter-bore would be formed in the top of the bur tube body which would accept the resilient washer. The retainer key would then be formed to be received in the counter bore and to form the top or upper surface of the bur tube. In another alternative for the retainer key, the transverse slot 54 of the bur tube can have inwardly sloping side walls rather than side walls that are parallel to the axis of the bur tube. The slot would then be generally trapezoidal or dove-tailed in shape, with the slot being narrower at the top than at the bottom. The retainer key 57 would be similarly shaped to be slid into the transverse slot 54. This dove-tailed or trapezoidal shape of the transverse slot and retainer key would prevent axial movement of the key 57 relative to the bur tube body 42. The bearing 45 would hold the key 57 against transverse movement. Thus, the key would not have to be welded or glued to the bur tube body, as is needed with the key that is generally rectangular in end elevation. These examples are merely illustrative.

I claim:

1. A medical/dental device including:

a body having a hollow sleeve and a head at an end of said sleeve, said sleeve receiving a drive mechanism, said head defining an upwardly opening chamber which is in communication with the hollow sleeve, said chamber having an upwardly opening mouth and a floor having an opening therethrough sized to admit the passage of a shaft of a medical/dental instrument; said shaft having an axis, a groove perpendicular to said axis, an axially extending flat surface generally parallel to the axis of the shaft and a shoulder at a bottom of said shaft flat surface extending generally perpendicular to the shaft axis;

a chuck which removably receives said shaft, said chuck including a bur tube which is rotatably received in said head, said shaft being receivable in said bur tube to be rotationally fixed relative to said bur tube to be driven by rotation of said bur tube; and a driven mechanism on said bur tube, said driven mechanism being operatively connected to said drive mechanism to be rotatably driven by said drive mechanism to rotate said bur tube and said bur;

said bur tube including:

a bur tube body having an upper surface and a bore which extends through said body sized to removably receive said shaft; a flexible arm including an inwardly extending finger positioned to engage said shaft groove when said shaft is inserted in said bur tube, said arm being movable between a first position in which said finger is received in said groove to prevent said shaft from being removed from said head and a second position in which said finger is disengaged from said groove to allow removal of said bur; an upper portion of said arm extending above the top of said shaft; and a resilient member extending into said bur tube bore; said resilient member having a bottom surface; said resilient member being shaped and sized to permit said flat surface of said shaft to pass above said resilient member; said shaft shoulder being in abutting relationship with said resilient member when said shaft is received in said bur tube.

2. The medical/dental device of claim 1 wherein said resilient member is a spring.

3. The medical/dental device of claim 1 wherein the bur tube includes a transverse slot in the bur tube body extending downwardly from the bur tube upper surface and a retaining key; the slot being sized and shaped to receive the retaining key and the resilient member; the retaining key being fixed in the bur tube body transverse slot above the resilient member to secure the resilient member in the slot.

4. The medical/dental device of claim 3 wherein said retaining key defines a chamber which is sized and shaped to receive the resilient member.

5. The medical/dental device of claim 1 wherein said bur tube is sized such than an upper portion of said shaft extends above said upper surface of said bur tube body to space said shaft groove above said bur tube body upper surface when said shaft is received in said bur tube, said flexible arm extending above said bur tube body upper surface.

6. The medical/dental device of claim 1 including a cap received in the mouth of said head and having an upper opening and a push button actuator accessible through said cap upper opening; said push button actuator being received in said cap and extending through said cap upper opening to be operable by a user of said medical/dental device, said push button actuator including a top, an annular wall depending from said top and having an inner surface, and a member depending from said push button top inside of said annular wall; said push button being axially slideable in said cap between a first position in which said member is spaced from said upper portion of said bur tube arm and a second position in which said member engages said upper portion of said bur tube arm to move said arm from said arm first position to said arm second position.

7. The medical/dental device of claim 6 wherein said push button member defines a truncated cone, said member having a sloped side which engages said bur tube arm upper portion to move said bur tube arm from its first position to its second position.

8. The medical dental device of claim 7 wherein said bur tube arm upper portion has a sloped upper surface, said sloped side of said member engaging said sloped surface of said arm upper portion.

9. The medical/dental device of claim 8 wherein said sloped side of said member has a length greater than the sloped surface of said arm upper portion.

10. The medical/dental device of claim 6 wherein said push button member has a lower surface, a bore being formed in said lower surface, said bore having a diameter at least as great as the diameter of said bur shaft at the top of said shaft and a depth sufficiently deep to prevent the top surface of said bur shaft from contacting said member when said push button is moved to its second position.

11. The medical/dental device of claim 1 wherein said bur tube has a wall and a axial slot extending downwardly from a top of said wall, said arm being positioned in said axial slot.

12. The medical/dental device of claim 11 wherein said arm has a width which is narrower than said axial slot and a depth, for at least a part thereof, which is narrower than the width of a wall of said bur tube.

13. The medical/dental device of claim 12 wherein the arm has an outer surface, said outer surface being curved to define a transition between a first portion of said arm where said arm has a thickness approximately equal to the width of said bur tube wall and a second portion of said arm where said arm has a thickness narrower than the bur tube wall.

14. The medical/dental device of claim 13 wherein the arm includes a third portion which extends above said finger, said arm third portion having a thickness narrower than the thickness of said arm second portion.

15. A bur tube for a medical/dental device which is adapted to removably receive a tool having a shaft, an axis and a groove spaced from the top of said shaft; the bur tube including a bur tube body having an upper surface, a bore which extends through said body, and a flexible arm having a finger, said finger having a flat upper surface; said bur tube further including a resilient member spaced from said bur tube body upper surface, said resilient member being received in a side wall of the bur tube and extending into said bur tube body bore and being shaped to exert an axial force on the tool when the tool is received in the bur tube.

16. A bur tube for a medical/dental device which is adapted to removably receive a tool having a shaft, an axis and a groove spaced from the top of said shaft; the bur tube including a bur tube body having an upper surface, a bore which extends through said body, and a flexible arm having a finger, said finger having a flat upper surface; said bur tube further including a resilient member which is spaced from said bur tube body upper surface and which extends into said bur tube body bore; and a retaining key; the bur tube body having a transverse slot extending downwardly from the bur tube body upper surface; the transverse slot being sized and shaped to receive the retaining key and the resilient member; the retaining key being fixed in the bur tube body transverse slot above the resilient member to secure the resilient member in the transverse slot.

17. The bur tube of claim 16 wherein said retaining key defines a chamber which is sized and shaped to receive the resilient member.

18. The bur tube of claim 17 wherein said resilient member is a leaf spring.

19. A medical/dental device including:

a body having a hollow sleeve and a head at an end of said sleeve, said sleeve receiving a drive mechanism, said head defining an upwardly opening chamber having a floor and an opening in said floor sized to admit the passage of a shaft of a medical/dental instrument, said shaft having an axis, a groove perpendicular to said axis spaced from a top of said shaft, and a shoulder generally perpendicular to said axis and spaced axially from said groove;

a chuck which removably receives said shaft, said chuck including a bur tube which is rotatably received in said head, said shaft being received in said bur tube to be rotationally fixed relative to said bur tube to be driven by rotation of said bur tube;

a driven mechanism on said bur tube, said driven mechanism being operatively connected to said drive mechanism to be rotatably driven by said drive mechanism to rotate said bur tube and said bur;

said bur tube including a bur tube body having a wall defining a bore which extends through said body sized to receive said shaft and an axially extending flexible arm; said flexible arm including an inwardly extending finger positioned to engage said shaft groove; said finger having a flat upper surface and a sloped lower surface, said arm being movable between a first position in which said finger is received in said shaft groove to prevent said shaft from being removed from said head and a second position in which said finger is disengaged from said groove to allow removal of said bur; said bur tube further including a resilient member which extends into said bur tube bore, said shoulder of said shaft abutting a lower surface of said resilient member when said shaft is received in said bur tube;

said shaft having a top edge which is beveled or rounded, said top edge of said shaft interacting with the sloped lower surface of said finger to urge said finger and said arm radially outwardly when said bur shaft is inserted into said head, said arm snapping from said second position to said first position when said groove comes into alignment with said finger.

20. The medical/dental device of claim 19 wherein the bur tube includes a transverse slot in the bur tube body extending downwardly from the bur tube upper surface and a retaining key; the transverse slot being sized and shaped to receive the retaining key and the resilient member; the retaining key being fixed in the bur tube body transverse slot above the resilient member to secure the resilient member in the transverse slot.

21. The medical/dental device of claim 20 wherein said retaining key defines a chamber which is sized and shaped to receive the resilient member.

22. The medical/dental device of claim 21 wherein said resilient member is a leaf spring.

23. A bur tube for a medical/dental device which is adapted to removably receive a tool having a shaft, an axis and a groove spaced from the top of said shaft; the bur tube including a bur tube body having an upper surface, a bore which extends through said body, and a flexible arm having a finger, said finger having a flat upper surface; said bur tube further including a leaf spring spaced from said bur tube body upper surface, said leaf spring extending across at least a portion of said bur tube bore to exert an axial force on said tool when said tool is inserted in said bur tube.

24. In combination, a bur tube for a medical/dental device and a medical/dental instrument which is removably received in the bur tube; the bur tube adapted to removably receive the medical/dental instrument, said instrument including a shaft having an axis, a groove perpendicular to the shaft axis, an axially extending flat surface generally parallel to the axis of the shaft and a shoulder at a bottom of said shaft flat surface extending generally perpendicular to the shaft axis; said bur tube including:

a bur tube body having an upper surface and a bore which extends through said body sized to removably receive said shaft; an inwardly extending finger positioned to engage said shaft groove when said shaft is inserted in said bur tube, and a resilient member extending into said bur tube bore; said resilient member having a bottom surface; said resilient member being shaped and sized to permit said flat surface of said shaft to pass above said bottom surface of said resilient member; said shaft shoulder being in abutting relationship with said resilient member when said shaft is received in said bur tube.

25. A bur tube for a medical/dental device which is adapted to removably receive a medical/dental instrument, said instrument including a shaft having an axis, a groove perpendicular to the shaft axis, an axially extending flat surface generally parallel to the axis of the shaft and a shoulder at a bottom of said shaft flat surface extending generally perpendicular to the shaft axis; said bur tube including a bur tube body having an upper surface, a bore which extends through said body sized to admit the medical/dental instrument therethrough, an arm having a finger adapted to engage the groove of the medical/dental instrument, and a moveable abutment surface below said finger, said abutment surface positioned to engage an instrument when the instrument is inserted in the bur tube to enable the bur tube to accept instruments which do not conform to standards.

26. The bur tube of claim 25 wherein the bur tube includes a resilient member having a bottom surface; the abutment surface comprises said bottom surfaces; said resilient member exerting an axial force on said medical/dental instrument.

\* \* \* \* \*